US012582332B2

(12) United States Patent
Chuo et al.

(10) Patent No.: US 12,582,332 B2
(45) Date of Patent: Mar. 24, 2026

(54) PIEZOELECTRIC SENSOR WITH RESONATING MICROSTRUCTURES

(71) Applicant: Apple Inc., Cupertino, CA (US)

(72) Inventors: Yindar Chuo, San Jose, CA (US); Zijing Zeng, San Jose, CA (US)

(73) Assignee: Apple Inc., Cupertino, CA (US)

( * ) Notice: Subject to any disclaimer, the term of this patent is extended or adjusted under 35 U.S.C. 154(b) by 837 days.

(21) Appl. No.: 17/355,442

(22) Filed: Jun. 23, 2021

(65) Prior Publication Data

US 2022/0409095 A1     Dec. 29, 2022

(51) Int. Cl.
| | |
|---|---|
| *A61B 5/11* | (2006.01) |
| *A61B 5/00* | (2006.01) |
| *A61B 7/00* | (2006.01) |
| *H10N 30/00* | (2023.01) |
| *H10N 30/30* | (2023.01) |

(52) U.S. Cl.
CPC .......... *A61B 5/1102* (2013.01); *A61B 5/6891* (2013.01); *A61B 7/003* (2013.01); *A61B 2562/028* (2013.01); *A61B 2562/066* (2013.01); *A61B 2562/18* (2013.01); *H10N 30/302* (2023.02); *H10N 30/704* (2024.05)

(58) Field of Classification Search
CPC ..... A61B 5/1102; A61B 5/6891; A61B 7/003; A61B 2562/028; A61B 2562/066; A61B 2562/18; H10N 30/1051; H10N 30/302; G01H 11/08
See application file for complete search history.

(56) References Cited

U.S. PATENT DOCUMENTS

| | | | |
|---|---|---|---|
| 3,209,380 | A | 10/1965 | Benjamin |
| 3,613,671 | A | 10/1971 | Poor et al. |
| 4,267,611 | A | 5/1981 | Agulnick |
| 4,827,763 | A | 5/1989 | Bourland et al. |

(Continued)

FOREIGN PATENT DOCUMENTS

| | | |
|---|---|---|
| CN | 104662800 | 5/2015 |
| CN | 205091721 | 3/2016 |

(Continued)

OTHER PUBLICATIONS

K.R. Rashmi, Arjun Sunil Rao, A. Jayarama, Richard Pinto; "Piezoelectric P(VDF-TrFE) micro cantilevers and beams for low frequency vibration sensors and energy harvesters;" Sensors and Actuators A: Physical, vol. 295, 2019, pp. 574-585. (Year: 2019).*

(Continued)

*Primary Examiner* — Jennifer Pitrak McDonald
*Assistant Examiner* — Christopher J Mutchler
(74) *Attorney, Agent, or Firm* — Brownstein Hyatt Farber Schreck, LLP

(57) ABSTRACT

A sensor system may have a force sensor formed from a piezoelectric film. The piezoelectric film may comprise a number of tuned microstructures that are configured to resonate at a particular frequency. In accordance with the tuning of the microstructures, frequency signals corresponding to the microstructure resonance may be mechanically amplified before being processed by associated processing electronics. The processing electronics may be configured to identify a type of biological vibration detected by the force sensor.

18 Claims, 11 Drawing Sheets

522

(56) References Cited

U.S. PATENT DOCUMENTS

| 5,385,036 | A | 1/1995 | Spillane et al. | |
| 5,389,848 | A | 2/1995 | Trzaskos | |
| 5,619,764 | A | 4/1997 | Lopau | |
| 5,638,565 | A | 6/1997 | Pekar | |
| 5,647,078 | A | 7/1997 | Pekar | |
| 5,651,151 | A | 7/1997 | Schild | |
| 6,415,467 | B1 | 7/2002 | Bretvin | |
| 6,564,410 | B2 | 5/2003 | Graebe et al. | |
| 6,679,315 | B2 | 1/2004 | Cosley | |
| 6,715,174 | B2 | 4/2004 | Tsai | |
| 6,827,128 | B2 | 12/2004 | Philpott et al. | |
| 7,007,330 | B2 | 3/2006 | Kuiper et al. | |
| 7,152,412 | B2 | 12/2006 | Harvie | |
| 7,325,455 | B2 | 2/2008 | Campbell et al. | |
| 7,395,717 | B2 | 7/2008 | DeAngelis et al. | |
| 7,492,241 | B2 | 2/2009 | Piazza et al. | |
| 7,500,536 | B2 | 3/2009 | Bulgajewski et al. | |
| 7,578,195 | B2 | 8/2009 | DeAngelis et al. | |
| 7,656,673 | B1 | 2/2010 | Fries et al. | |
| 7,712,373 | B2 | 5/2010 | Nagle et al. | |
| 7,948,315 | B2 | 5/2011 | Shifrin | |
| 8,169,124 | B2 | 5/2012 | Lee et al. | |
| 8,258,675 | B2 | 9/2012 | Ikehara et al. | |
| 8,341,786 | B2 | 1/2013 | Oexman | |
| 8,353,207 | B2 | 1/2013 | Hakansson | |
| 8,426,933 | B2 | 4/2013 | Yacoubian | |
| 8,540,644 | B2 | 9/2013 | Husheer | |
| 8,598,893 | B2 | 12/2013 | Camus | |
| 8,768,520 | B2 | 7/2014 | Oexman et al. | |
| 8,771,204 | B2 | 7/2014 | Telfort et al. | |
| 8,917,167 | B1 | 12/2014 | Selker | |
| 8,961,904 | B2 | 2/2015 | Xia | |
| 8,979,766 | B2 | 3/2015 | Sullivan | |
| 8,997,588 | B2 | 4/2015 | Taylor | |
| 9,015,885 | B2 | 4/2015 | Chapin | |
| 9,131,039 | B2 | 9/2015 | Behles | |
| 9,216,122 | B2 | 12/2015 | Dzioba et al. | |
| 9,271,665 | B2 | 3/2016 | Sarrafzadeh et al. | |
| 9,278,629 | B2 | 3/2016 | Stanley et al. | |
| 9,354,703 | B2 | 5/2016 | Maggiali et al. | |
| 9,504,416 | B2 | 11/2016 | Young | |
| 9,542,028 | B2 | 1/2017 | Filiz et al. | |
| 9,591,995 | B2 | 3/2017 | Blumberg | |
| 9,652,101 | B2 | 5/2017 | McMillen | |
| 9,723,719 | B2 | 8/2017 | DeRosa et al. | |
| 9,733,136 | B2 | 8/2017 | Seitz | |
| 9,848,494 | B2 | 12/2017 | Huitema et al. | |
| 9,848,712 | B2 | 12/2017 | Main et al. | |
| 9,852,656 | B2 | 12/2017 | Ander et al. | |
| 9,857,930 | B2 | 1/2018 | Sebastian et al. | |
| 10,178,472 | B1 * | 1/2019 | Rhee | H04R 7/06 |
| 10,180,721 | B2 | 1/2019 | Hoen et al. | |
| 10,219,749 | B2 | 3/2019 | Kim | |
| 10,258,535 | B2 | 4/2019 | Lem et al. | |
| 10,278,638 | B2 | 5/2019 | Dusanter et al. | |
| 10,305,017 | B2 | 5/2019 | Kondo | |
| 10,314,407 | B1 | 6/2019 | Main et al. | |
| 10,338,755 | B2 | 7/2019 | Podhajny et al. | |
| 10,349,895 | B2 | 7/2019 | Telfort et al. | |
| 10,416,031 | B2 | 9/2019 | Hsu et al. | |
| 10,418,933 | B2 | 9/2019 | France et al. | |
| 10,463,340 | B2 | 11/2019 | Telfort et al. | |
| 10,561,253 | B2 | 2/2020 | Tsern et al. | |
| 10,653,332 | B2 | 5/2020 | McGrane et al. | |
| 10,763,421 | B2 | 9/2020 | Benedict et al. | |
| 10,765,409 | B2 | 9/2020 | Lafon et al. | |
| 10,768,066 | B2 | 9/2020 | Kamiya et al. | |
| 10,779,802 | B2 | 9/2020 | Tholen et al. | |
| 10,888,268 | B2 | 1/2021 | Baltay et al. | |
| 10,925,573 | B2 | 2/2021 | Martin et al. | |
| 11,020,298 | B2 | 6/2021 | Brykalski | |
| 11,105,025 | B2 | 8/2021 | Boylu et al. | |
| 11,191,486 | B2 | 12/2021 | Griffin et al. | |
| 11,219,397 | B2 | 1/2022 | Wang et al. | |
| 11,253,079 | B1 | 2/2022 | Kahn | |
| 11,259,742 | B2 | 3/2022 | Etleb et al. | |
| 11,311,111 | B2 | 4/2022 | Grutta et al. | |
| 11,462,673 | B2 | 10/2022 | Yoshida et al. | |
| 11,540,416 | B2 | 12/2022 | Mou et al. | |
| 11,554,065 | B2 | 1/2023 | Chee | |
| 11,642,077 | B2 | 5/2023 | Ramirez et al. | |
| 11,679,047 | B2 | 6/2023 | Wijesundara | |
| 11,860,048 | B2 | 1/2024 | Bao et al. | |
| 2005/0257822 | A1 | 11/2005 | Smith et al. | |
| 2009/0058232 | A1 * | 3/2009 | Takahashi | H03H 9/21 29/25.35 |
| 2009/0093687 | A1 | 4/2009 | Telfort et al. | |
| 2010/0094139 | A1 | 4/2010 | Brauers et al. | |
| 2011/0107521 | A1 | 5/2011 | Alder et al. | |
| 2011/0296621 | A1 | 12/2011 | McKenna | |
| 2012/0242492 | A1 | 9/2012 | Grunfeld | |
| 2012/0313420 | A1 | 12/2012 | Beyerlein et al. | |
| 2015/0137994 | A1 | 5/2015 | Rahman et al. | |
| 2015/0164409 | A1 | 6/2015 | Benson et al. | |
| 2016/0317370 | A1 | 11/2016 | Evans et al. | |
| 2016/0370210 | A1 | 12/2016 | Kapusta et al. | |
| 2017/0056644 | A1 | 3/2017 | Chahine et al. | |
| 2017/0228072 | A1 * | 8/2017 | Amin | H10N 30/853 |
| 2018/0184920 | A1 | 7/2018 | Rabinovich et al. | |
| 2018/0254403 | A1 | 9/2018 | Jeong et al. | |
| 2019/0109904 | A1 | 4/2019 | Binder et al. | |
| 2019/0117165 | A1 | 4/2019 | Zeng et al. | |
| 2019/0187794 | A1 | 6/2019 | Khoshkava | |
| 2019/0223736 | A1 | 7/2019 | Wang et al. | |
| 2019/0360880 | A1 * | 11/2019 | Li | G01L 1/162 |
| 2019/0368087 | A1 | 12/2019 | Boylu et al. | |
| 2020/0178827 | A1 | 6/2020 | Correa Ramirez et al. | |
| 2020/0295250 | A1 * | 9/2020 | Li | H03H 9/02244 |
| 2021/0038092 | A1 | 2/2021 | Amin et al. | |
| 2021/0041287 | A1 | 2/2021 | Rimminen et al. | |
| 2021/0085091 | A1 | 3/2021 | Brandt et al. | |
| 2021/0169233 | A1 | 6/2021 | Tsern et al. | |
| 2021/0295661 | A1 | 9/2021 | Tadele et al. | |
| 2021/0356345 | A1 | 11/2021 | Li et al. | |
| 2022/0047250 | A1 | 2/2022 | Clements et al. | |
| 2022/0061699 | A1 | 3/2022 | LaBove et al. | |
| 2023/0083674 | A1 * | 3/2023 | Li | H10N 30/302 310/311 |
| 2023/0292620 | A1 * | 9/2023 | Polesel | H10N 30/076 |
| 2024/0427421 | A1 | 12/2024 | Tadele et al. | |

FOREIGN PATENT DOCUMENTS

| CN | 106618521 | | 5/2017 | |
| CN | 107111411 | | 8/2017 | |
| CN | 109642833 | | 4/2019 | |
| CN | 110072432 | | 7/2019 | |
| CN | 110381817 | | 10/2019 | |
| CN | 111051834 | | 4/2020 | |
| CN | 111061944 | | 4/2020 | |
| CN | 111372547 | | 7/2020 | |
| CN | 213182667 | | 5/2021 | |
| CN | 111504443 | B * | 11/2024 | H10N 30/09 |
| EP | 2967225 | | 6/2017 | |
| JP | H08131408 | | 5/1996 | |
| JP | 2003164527 | | 6/2003 | |
| JP | 2006230790 | | 9/2006 | |
| JP | 2008264352 | | 11/2008 | |
| JP | 2010502338 | | 1/2010 | |
| JP | 2014212977 | | 11/2014 | |
| JP | 2019051069 | | 4/2019 | |
| KR | 20140005289 | | 1/2014 | |
| KR | 101841365 | | 3/2018 | |
| KR | 20180079957 | | 7/2018 | |
| KR | 102087286 | | 4/2020 | |
| WO | 2005/031300 | * | 4/2005 | |
| WO | WO 14/067777 | | 5/2014 | |
| WO | WO 16/019087 | | 2/2016 | |
| WO | WO 17/190085 | | 11/2017 | |
| WO | WO 18/023135 | | 2/2018 | |
| WO | WO 19/073104 | | 4/2019 | |

(56)            References Cited

FOREIGN PATENT DOCUMENTS

WO      WO 20/073091      4/2020
WO      WO 21/087326      5/2021

OTHER PUBLICATIONS

Yi-Yuan Chiu, Wan-Ying Lin, Hsin-Yao Wang, Song-Bin Huang, Min-Hsien Wu; "Development of a piezoelectric polyvinylidene fluoride (PVDF) polymer-based sensor patch for simultaneous heartbeat and respiration monitoring;" Sensors and Actuators A: Physical, vol. 189, 2013, pp. 328-334. (Year: 2013).*

Janusas G, Ponelyte S, Brunius A, Guobiene A, Prosycevas I, Vilkauskas A, Palevicius A. Periodical Microstructures Based on Novel Piezoelectric Material for Biomedical Applications. Sensors (Basel). Dec. 15, 2015;15(12):31699-708. (Year: 2015).*

M. Komeili, A. Ahrabi, and C. Menon, "Resonance vibration of an optical fiber micro-cantilever using electro-thermal actuation," Mathematical Models in Engineering, vol. 3, No. 1, pp. 1-16, Jun. 2017, (Year: 2017).*

Tiffany C. Kaspar et al.; "Tuning piezoelectric properties through epitaxy of La2Ti2O7 and related thin films;" Scientific Reports(2018) 8:3037 (Year: 2018).*

Wikipedia, "Cantilever," https://en.wikipedia.org/wiki/Cantilever; Accessed Apr. 18, 2024 (Year: 2024).*

Merriam Webster Online Disctionary, "Definition: Microstructure," https://www.merriam-webster.com/dictionary/microstructure; accessed Aug. 14, 2024. (Year: 2024).*

Wikipedia, "Resonance," https://en.wikipedia.org/wiki/Resonance, accessed Aug. 14, 2024 (Year: 2024).*

Robertson et al., "A Compact Modular Soft Surface with Reconfigurable Shape and Stiffness," IEEE/ASME Transactions on Mechatronics, vol. 24, No. 1, Feb. 2019, pp. 16-24.

U.S. Appl. No. 17/871,605, filed Jul. 22, 2022, Brandt et al.

U.S. Appl. No. 18/687,201, filed Feb. 27, 2024, Tadele et al.

Dorfmeister et al., "A Novel Bi-Stable MEMS Membrane Concept Based on a Piezoelectric Thin Film Actuator for Integrated Switching," vol. 2, No. 912; doi:10.3390/proceedings2130912, Proceedings 2018.

Phelps, Isaac James, "Mechanical characterization of MEMS bistable buckled diaphragms," University of Louisville, Electronic Theses and Dissertations, Paper 1129, 2013.

* cited by examiner

650

A

B

606

614a
615a
616a
615b
620a
615c
622
615d
620b
615e
616b
615f
614b

900

PIEZOELECTRIC SENSOR WITH RESONATING MICROSTRUCTURES

FIELD

Embodiments described herein generally relate to force sensors, vibration sensors, piezoelectric sensors, and/or to a sensor system including such sensors. The sensor or sensor system may be or include a piezoelectric force sensor and may be used on a bed or elsewhere to sense vibrations, including vibrations generated through sounds. The sensed vibrations may include biological vibrations or sounds made by a user, such as heart vibrations and/or lung vibrations. In particular, a force sensor may include resonating microstructures to mechanically amplify vibrational signals within specific biological ranges of interest while the vibrational signals are being collected.

BACKGROUND

During the course of everyday life, a person may create a number of vibrations or sounds related to biometric activity including, for example, vibrations and/or sounds coming from the lungs and/or the heart. Various sensing devices, including various health sensors, may be capable of monitoring a user's heart rate, heart rhythm, steps taken, calories burned, and so on as the user interacts with the sensing devices. However, certain vibrations within certain frequency ranges may be difficult to detect, particularly if the vibrations have a low amplitude and/or if the vibrations are overpowered by other vibrations. Although the vibrations may be captured by the various sensing devices, vibrational data may be hidden behind noise and/or may otherwise be difficult to analyze.

SUMMARY

This summary is provided to introduce a selection of concepts that are further described herein. This summary is not intended to identify key features or essential features of the claimed subject matter, nor is it intended to be used as an aid in determining the scope of the claimed subject matter.

Disclosed herein are sensor systems for sensing a biological vibration. The sensor system may comprise a sensor stack. The sensor stack may comprise a piezoelectric film having a first side opposing a second side and comprising an array of microstructures, each microstructure of the array of microstructures being tuned to resonate within a biological range of interest corresponding to the biological vibration, a first electrode connected to the first side of the piezoelectric film, and a second electrode connected to the second side of the piezoelectric film, the first electrode and the second electrode converting the biological vibration detected by at least one microstructure of the array of microstructures into electrical signals.

In some embodiments, each microstructure of the array of microstructures may have a cantilever structure and the cantilever structure may be tuned to amplify detection of the biological vibration.

In some embodiments, the sensor stack further comprises a first shielding film coupled to the first electrode and a second shielding film coupled to the second electrode. The first electrode may be disposed between the piezoelectric film and the first shielding film and the second electrode may be disposed between the piezoelectric film and the second shielding film.

In some embodiments, the array of microstructures may be a first array of first microstructures. The biological range of interest may be a first biological range of interest. The piezoelectric film may further comprise a second array of second microstructures. Each of the second array of second microstructures may be tuned to a second biological range of interest. The second biological range of interest may be different from the first biological range of interest.

The first biological range of interest may correspond to lung vibrations in a first range of 50 Hertz to 2500 Hertz. The second biological range of interest may correspond to heart vibrations in a second range of 20 Hertz to 500 Hertz.

The first array of first microstructures and the second array of second microstructures may be formed in an alternating pattern on the piezoelectric film.

The first array of first microstructures may be formed within a first area of the piezoelectric film. The second array of second microstructures may be formed within a second area of the piezoelectric film. The first area may not overlap with the second area.

The array of microstructures may be formed as a repeating grid of microstructures on the piezoelectric film.

The piezoelectric film may be formed from a polyvinylidene difluoride material. The sensor system may further comprise a communications interface configured to transmit the electrical signals to an external electronic device.

A sensor system for monitoring biological vibrations generated by a user may be provided. The sensor system may comprise a flexible sensor detecting the biological vibrations from the user while the user is in contact with the flexible sensor. The flexible sensor may comprise a flexible piezoelectric film comprising an array of microstructures, each microstructure of the array of microstructures defining a respective hole of the flexible piezoelectric film and having a respective cantilevered structure amplifying detected vibrations within a biological range of interest, a first electrode and a second electrode, respectively connected to a first surface of the piezoelectric film and a second surface of the piezoelectric film, the first surface opposing the second surface, and a differential amplifier electrically connected to the first electrode and the second electrode and providing a differential output indicative of the detected vibrations sensed by the array of microstructures of the piezoelectric film.

In some embodiments each microstructure of the array of microstructures may be tuned to resonate at a frequency corresponding to at least one of heart vibrations or lung vibrations. The array of microstructures may be more concentrated at a center portion of the piezoelectric film than at an edge portion of the piezoelectric film.

In some embodiments, the array of microstructures may comprise a first set of microstructures comprising first microstructures and a second set of microstructures comprising second microstructures. The first microstructures may have a larger size than the second microstructures.

In some embodiments, the first set of microstructures may be positioned at an edge portion of the piezoelectric film and the second set of microstructures may be positioned at a center portion of the piezoelectric film. The array of microstructures may additionally comprise a third set of microstructures comprising third microstructures and the third microstructures may have a smaller size than the first microstructures and the second microstructures.

In some embodiments, the first microstructures of the first set of microstructures may be tuned to detect first frequencies within a first biological range of interest, the second microstructures of the second set of microstructures may be tuned to detect second frequencies within a second biological range of interest, the second frequencies higher than the first frequencies, and the third microstructures of the third set of microstructures may be tuned to detect third frequencies within a third biological range of interest, the third frequencies higher than the second frequencies.

A method of monitoring vibrations generated by a user may additionally be provided. The method may comprise receiving a first signal from a pair of electrodes, each electrode of the pair of electrodes connected to opposite sides of a piezoelectric element, the first signal generated by first vibrations of a first array of microstructures of the piezoelectric element, receiving a second signal from the pair of electrodes, the second signal generated by second vibrations of a second array of microstructures of the piezoelectric element, determining a first type of biological vibration corresponding to the first signal, determining a second type of biological vibration corresponding to the second signal, the second type of biological vibration different from the first type of biological vibration, and, based on the first type of biological vibration, the second type of biological vibration, the first signal, and the second signal, generating an output that reports a health condition of the user over a period of time.

In some embodiments, the first type of biological vibration may correspond to a lung sound and/or vibration and the second type of biological vibration may correspond to a heart sound and/or vibration.

In some embodiments, the first signal and the second signal may be mechanically pre-amplified, by the first array of microstructures and the second array of microstructures, with respect to a flat response of the piezoelectric element.

BRIEF DESCRIPTION OF THE DRAWINGS

Reference will now be made to representative embodiments illustrated in the accompanying figures. It should be understood that the following descriptions are not intended to limit the embodiments to one or more preferred embodiments. To the contrary, they are intended to cover alternatives, modifications, and equivalents as may be included within the spirit and scope of the described embodiments as defined by the appended claims. Similar reference numerals have been used, where practicable, to designate similar features.

Figure 1:
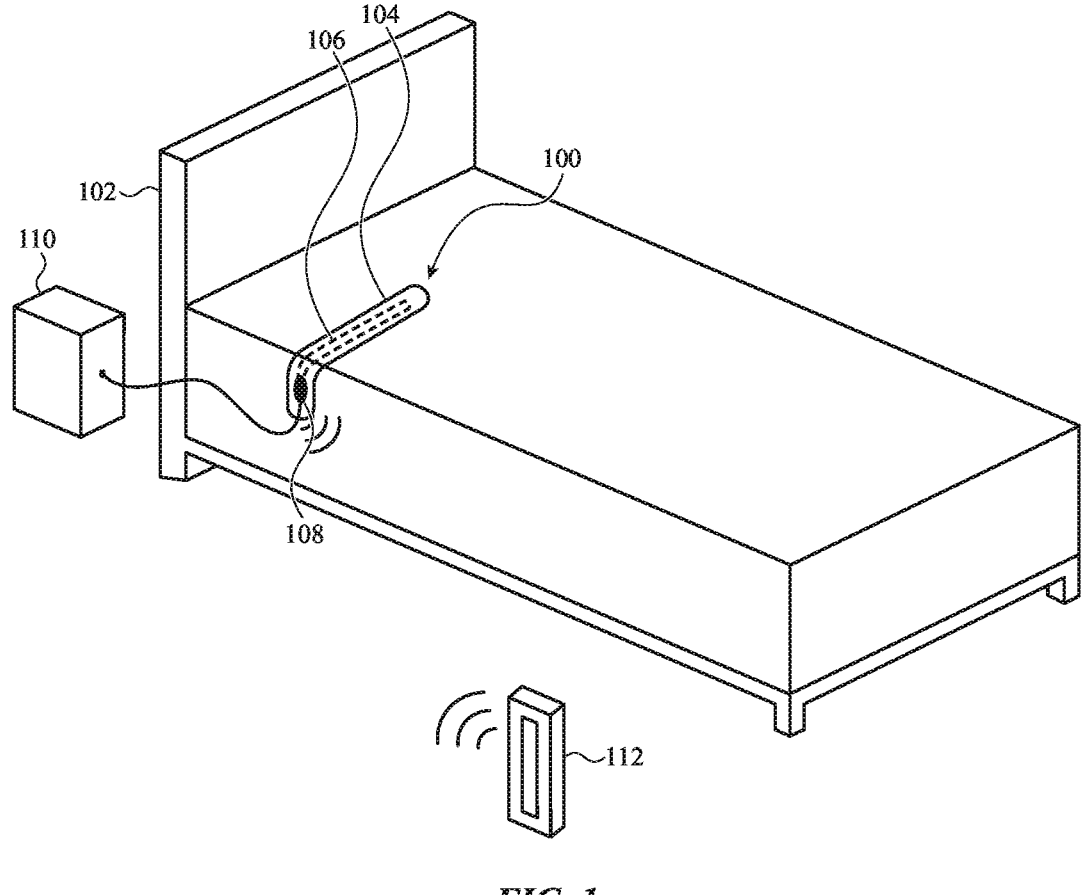
FIG. 1 depicts an example sensor system, including a force sensor, that may be used to detect and monitor biological vibrations.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Described herein are sensors, such as force sensors and/or vibration sensors, that collect biological vibrations, such as heart vibrations or sounds, lung vibrations or sounds, nasal vibrations or sounds, digestive vibrations or sounds, and so on. Particular types of biological vibrations commonly occur within a particular frequency range or "band." For example, chest cavity vibrations, such as heart and lung vibrations or sounds, commonly occur within a band of about 5 Hertz (Hz) to about 1 kilohertz (kHz). These chest cavity vibrations may be considered a "biological range of interest" corresponding to particular vibrational signal bands. In some cases, biological ranges of interest correspond to other biological vibrations, such as vibrations arising from blood flow and/or vibrations arising from general movements; to heart vibrations; to lung vibrations; and/or to any other type of vibration. It may additionally be appreciated that any particular biological range of interest, as discussed with respect to biological vibrations, are disclosed for explanatory purposes and may differ or vary across individual users.

Force sensors, and particularly force sensors adapted to collect biological vibrations, may sense and/or detect vibrations that are generally too small in amplitude to be detected by a person. In some cases, the force sensor detect vibrations within a particular biological range of interest. However, in some situations, competing vibrations mask or otherwise de-emphasize vibrations within the biological range of interest. For example, ambient sounds, furniture and/or bed vibrations, appliance noise, and user movement produce vibrations with an amplitude/intensity in excess of vibrations within the biological range of interest. This effect may be particularly pronounced in force sensors having a flat sensor response. In some cases, a flat sensor response occurs due to a flat geometry of the force sensor such as, for example, a force sensor using a flat film layer with no significant resonances. Where significant noise is present, certain force sensing systems may isolate signals within the biological range of interest by performing post-processing of vibrational signals. However, post-processing may be time-intensive, may produce noisy data, and/or may require relatively large amounts of power. In addition, a flat sensor response may result in a force sensor which is unable to appreciably detect signals below a certain frequency response threshold, as increasing a sensitivity of such a force sensor may result in excess noise. It is noted that, in some cases, the force sensors described herein detect vibrations, corresponding to periodic oscillations, and non-oscillating forces, such as a strike. It is additionally noted that vibrations may include oscillating forces such as, for example, oscillating pressure waves coming into contact with a force sensor. For simplicity, the disclosure references force sensors which detect vibrations, though it is noted that additional and/or alternative forces may be detected by a force sensor.

By contrast, embodiments of a force sensor, as described herein, may include mechanical microstructures configured to vibrate at predetermined resonant frequencies, thereby providing mechanical amplification of vibrational signals within a biological range of interest. In some embodiments, a force sensor incorporates a piezoelectric film between electrode electronics.

In some cases, microstructures are formed from, or with respect to, a surface of the piezoelectric film and these microstructures resonate at predetermined frequencies. Insofar as the microstructures have a predetermined resonant frequency, the microstructures may vibrate more strongly in response to certain biological vibrations so as to amplify some detected frequencies within a particular biological range of interest. That is, the resonant frequency of a particular microstructure may be tuned to be within a biological range of interest such that the particular microstructure is more sensitive to vibrations with the biological range of interest. In this way, the particular microstructure may amplify vibrations within the biological range of interest, as discussed herein.

In some cases, the microstructures are tuned to a particular resonant frequency at a time of manufacture of a force sensor and/or piezoelectric film. In some cases, microstructures include cantilevered piezoelectric film segments, the vibrations of which may be detectable by electrodes and/or sensing electronics of a force sensor. Due to the mechanical structure of such microstructures, the associated force sensor may have an increased dynamic range and may be able to amplify vibrations within a biological range of interest even if such vibrations have a relatively low intensity. Due to this mechanical pre-amplification, vibrations within the biological range of interest may be more easily detected and analyzed.

As discussed herein, the piezoelectric film may include a set of cantilevered piezoelectric film segments, which may be otherwise referenced as cantilever segments and/or cantilever structures. In some cases, the cantilever structures have four sides, where one side (e.g., a supported side) is joined to a piezoelectric film and the other three sides are unsupported and surrounded by empty space. When a vibration occurs, the cantilever structures may vibrate, or otherwise move, about the supported side. In some cases, the physical structure of the cantilever structures may be tuned, or changed, such that the cantilever structures resonate within a particular frequency range, which may correspond to a biological range of interest. For example, a thickness or dimension of the cantilever structures can be changed to tune the cantilever structures. In some cases, multiple cantilever structures may be tuned differently, so that a first set of cantilever structures of a force sensor resonate within a first biological range of interest and a second set of cantilever structures resonate within a second biological range of interest.

These and other techniques are described with reference to FIGS. 1-9. However, those skilled in the art will readily appreciate that the detailed description given herein with respect to these figures is for explanatory purposes only and should not be construed as limiting.

Directional terminology, such as "top," "bottom," "upper," "lower," "front," "back," "over," "under," "left," "right," and so on, is used with reference to the orientation of some of the components in some of the figures described below. Because components in various embodiments can be positioned in a number of different orientations, directional terminology is used for purposes of illustration only and is not limiting. The directional terminology is intended to be construed broadly, and therefore should not be interpreted to preclude components being oriented in different ways. The use of alternative terminology, such as "or," is intended to indicate different combinations of the alternative elements. For example, A or B is intended to include, A, or B, or A and B.

FIG. 1 depicts an example sensing package 100 as provided on a bed 102, an external electronic device 112, and a power supply 110. The sensing package 100 may be used to detect biological vibrations, such as chest cavity vibrations or sounds, nasal cavity vibrations or sounds, abdominal cavity vibrations or sounds, and so on, made by a person lying on the bed 102. In some cases, the sensing package 100 includes additional sensors or associated objects, such as, for example, a temperature sensor, a strain gauge, and processing electronics.

Discussed generally, the sensing package 100 may be installed on a bed 102. The sensing package 100 may include a housing 104, a force sensor 106 positioned within the housing 104, and processing circuitry 108 communicatively coupled with the force sensor 106. When a person lies on the bed 102, the person may also lie on at least a portion of the sensing package 100. The person may further produce one or more biological vibrations as, for example, the person breathes or moves. The produced biological vibrations may be detected by the force sensor 106 which, in some embodiments, includes resonant microstructures designed to amplify vibrations in a particular biological range of interest. The vibrations, as detected by the force sensor, may be converted to electrical signals by the force sensor 106, via, for example, a set of electrodes, and may be transmit to processing circuitry 108. The processing circuitry 108 may further amplify, modulate, or otherwise influence the received electrical signals and may transmit signals to an electronic device 112. The person may then interact with the electronic device 112 to view, for example, data or graphs derived from the biological vibrations detected by the force sensor 106. In some embodiments, a report detailing the users biological vibrations and sleep quality is displayed via the electronic device 112.

As depicted in FIG. 1, the sensing package 100 includes a housing 104, a force sensor 106, and processing circuitry 108. The sensing package 100 can be used with any piece of furniture or object to detect vibrations, and, in some cases, to detect biological vibrations. In some cases, the sensing package 100 is provided on a chair, a couch, a table, a carpet, a sheet, any other object which a person interacts with, and so on. In some cases, the sensing package 100 is provided on a surface where a user commonly sits, stands, or lays. In the example depicted in FIG. 1, the sensing package 100 is provided on a bed 102 to detect biological vibrations while a person is sleeping, or laying, on the bed 102.

As depicted in FIG. 1, the sensing package 100 includes a first portion that rests on a top surface of the bed 102 and a second portion that hangs over an edge of the bed 102. However, in additional or alternative cases, the entirety of the sensing package may rest on the top surface of the bed.

In alternative or additional cases, the sensing package 100 may be used by a person who has attached part or all of the sensing package 100 (e.g., the housing 104) to their torso, or to an object, such as an article of clothing, in contact with their torso. The sensing package 100 may detect any type of vibration, including biological vibrations, which are applied either directly to the sensing package 100 or to an object on which the sensing package 100 is located (e.g., the bed 102).

In some embodiments, the sensing package 100 includes a force sensor 106 that is coupled to processing circuitry 108. The force sensor 106 may additionally be referenced as a vibration sensor, such as discussed herein. As depicted in FIG. 1, the force sensor 106 and the processing circuitry 108 are housed in a housing 104 of the sensing package 100. In alternative or additional cases, the processing circuitry 108 may be provided outside of the housing 104 and may, in some cases, be provided in a separate electronic device 112. The force sensor 106 may be coupled to the processing circuitry 108 wirelessly; by wires, conductive traces, or other conductive elements, which may be disposed on a printed circuit board (PCB) or integrated circuitry; and/or by any combination thereof.

In some cases, the sensing package 100 is flexible. For example, the housing 104 and the force sensor 106 may be flexible in order to be nearly or entirely imperceptible to a person lying on the bed 102. In some cases, the housing 104 and/or the force sensor 106 are formed partially or entirely from fabric and may include metallic and/or conductive traces woven into the fabric. Further, the processing circuitry 108 may also be flexible. For example, the processing circuitry 108 may be formed on a flexible substrate.

In some cases, the sensing package 100 is not flexible and is instead at least partially rigid relative to a surrounding surface (e.g., the bed 102). In some cases, certain components of the sensing package 100, such as the housing 104 and the force sensor 106, are at least partially flexible and other components of the sensing package 100, such as the processing circuitry 108, are at least partially rigid with respect to the flexible components. For example, first components of the sensing package 100 in contact with a top surface of the bed 102 can be made flexible, as a person directly or indirectly comes into contact with the first components during sleep, and second components hanging off the bed 102 can be made inflexible, or rigid, as a person rarely or never comes into contact with the second components during sleep.

The processing circuitry 108 may receive and process signals received from the force sensor 106. For example, the processing circuitry 108 may amplify and digitize signals received from the force sensor 106. In some cases, the processing circuitry 108 comprises a communications interface for communicating digitized signals or other information to an electronic device 112, such as a mobile phone or electronic watch. The communications interface may also receive signals, such as control signals, from the electronic device 112. For example, the communications interface can receive instructions, control signals, settings, or queries from the electronic device 112. The communications interface may transmit signals via wireless protocols, such as WI-FI or BLUETOOTH, or wired connections, such as a universal serial bus (USB) interface, an 8-pin connector, and so on. In some cases, the processing circuitry 108 includes one or more processors, such as a microprocessor, a microcontroller, an application-specific integrated circuit (ASIC), a field-programmable gate array (FPGA), and so on. The processor may control operations of the processing circuitry 108 including processing signals from the force sensor 106 and/or from the communications interface. In some cases, part or all of the processing circuitry 108 is integrated with the force sensor 106 on a shared substrate. In some embodiments, components or functions of the processing circuitry 108 are housed by, or provided by, the electronic device 112.

In some cases, the housing 104 encloses the force sensor 106, protects the force sensor 106 from dust, oil, moisture, or liquid spills, and/or electrically insulate the force sensor 106 from a user. In some embodiments, the housing 104 is formed from natural or synthetic cloth, plastic, or other materials, and comprises a sealed or accessible pouch configured to hold the force sensor 106. In some cases, the housing 104 is integrated with, or formed from, a bed sheet, mattress, cushion, or seating surface. In some cases, the housing 104 is formed from a polymer, thermoplastic polymer, resin, or other material that is applied to, encapsulates, or is molded around the force sensor 106. In some cases, the housing 104 incorporates or is formed from both an inner package, such as a material that is applied to, encapsulates, or is molded around the force sensor 106, and an outer package, such as a cloth, plastic sleeve, or cover.

A power supply 110 may additionally be communicatively coupled to the sensing package 100 and/or to the processing circuitry 108. In some cases, the power supply 110 is an external power supply such as a generator or a battery. In additional or alternative embodiments, the power supply 110 represents a plug that can be coupled with an outlet to receive power from a municipal power supply such as a powerplant. Further, the power supply 110 may be an integrated battery and may be provided within the housing 104 as part of the sensing package 100. In such cases, the power supply 110 may be rechargeable and may be fixed to, or detachable from, a recharging station. In instances where the power supply 110 is detachable, the power supply 110 may be replaceable batteries. Though the power supply 110 is depicted with a particular size in FIG. 1, the power supply 110 may be any size including sizes smaller than the processing circuitry 108.

Figure 2:
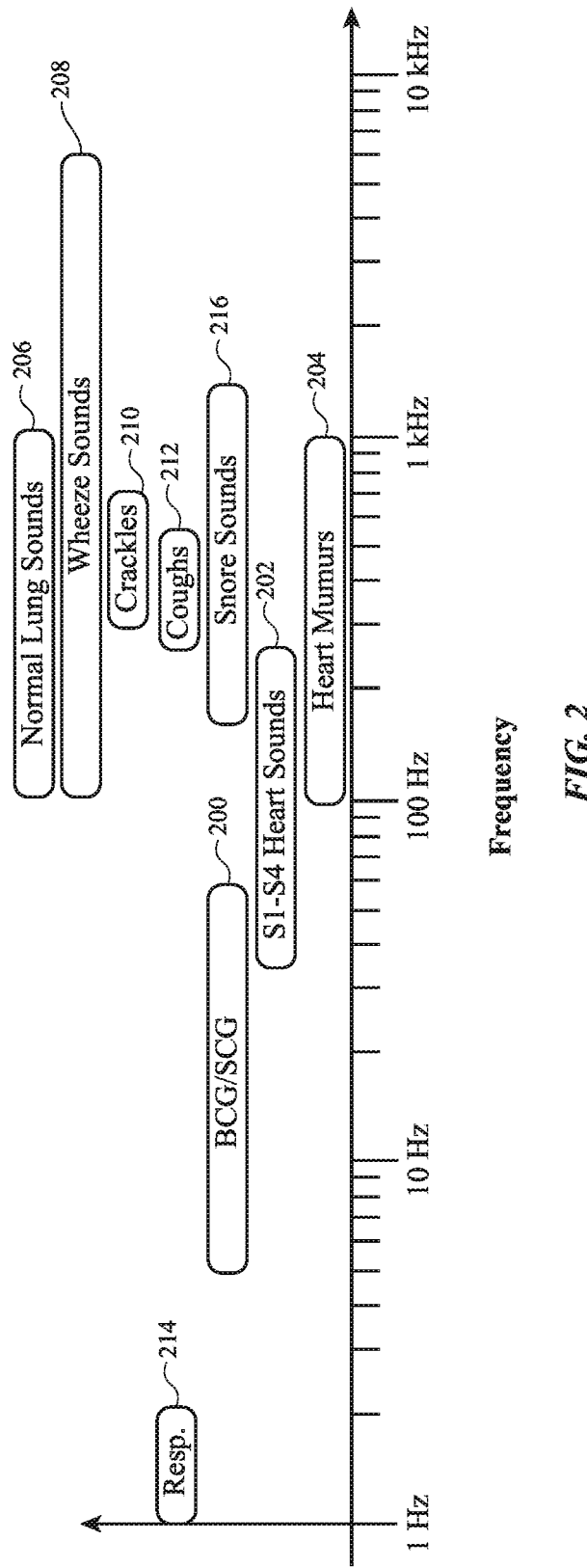
FIG. 2 depicts a chart including examples of different types of biological vibrations along with approximate biological ranges of interest corresponding to each depicted type of biological vibration.

FIG. 2 illustrates examples of different types of biological vibrations that may be detected by the force sensor 106, as described with reference to FIG. 1, and the approximate frequency ranges, or biological range of interest, of such vibrations.

For example, heart vibrations or sounds can be sensed by a force sensor. Heart vibrations and sounds include: ballistocardiogram (BCG) and/or seismocardiogram (SCG) vibrations and sounds 200 extending from about 5 Hz-50 Hz; S1 (a first heart sound), S2 (a second heart sound), S3 (a third heart sound), and S4 (a fourth heart sound) heart sounds 202 extending from about 25 Hz-250 Hz; and heart murmurs 204 (including different types of heart murmurs) extending from about 100 Hz-1 kHz.

Lung vibrations or sounds may additionally be sensed by a force sensor. Lung vibrations and sounds include: normal lung sounds 206; wheeze sounds 208; crackle sounds 210; and cough sounds 212. Normal lung sounds 206, such as vesicular sounds, may generally extend from about 100 Hz-1 kHz; wheeze sounds 208 may generally extend from about 100 Hz-5 kHz; crackle sounds 210 may generally extend from about 300 Hz-700 Hz; and cough sounds 212 may generally extend from about 275 Hz-600 Hz. Respiration vibrations 214, such as inspiration and expiration vibrations, are generally in the 1 Hz-2 Hz range, and are typically not audible to the human ear.

Further, nasal vibrations or sounds may be sensed by a force sensor. Nasal vibrations and sounds include snore sounds 216. Snore sounds 216 may generally extend from about 130 Hz-1.25 kHz.

Each of the above frequency ranges may correspond to a particular biological range of interest, as discussed herein. For example, a first biological range of interest can correspond to S1, S2, S3, and S4 heart sounds and a second biological range of interest can correspond to heart murmurs.

In some implementations, a type of biological vibration that is sensed by a force sensor is distinguished based on a biological range of interest within which the sensed biological vibration falls. Additionally or alternatively, biological vibration types can be distinguished by any or all of: their vibration patterns; a combination of their frequency bandwidth and vibration pattern; or using alternative or additional parameters, such as peak-to-peak timings, peak-to-peak intensities, and so on. However, the vibration patterns for the different biological sound types may vary, in some cases substantially, for different people and/or during different time periods.

The force sensor (e.g., processing electronics of the force sensor) may make a determination as to what type of biological vibration is being or has been detected. For example, if a vibration within a biological range of interest corresponding to heart murmurs is detected, the force sensor may determine that the detect vibration is a heart murmur. After this determine, the force sensor may output the determination to a user via, for example, a communications interface and/or an electronic device. Based on the type of biological vibration, the force sensor may generate an output, such as a report, graph, and so on, to provide sensor data to a user or device.

The force sensor may, for example, use detected signals and determined types of biological vibrations to generate a graph tracking various health conditions of a user during a specified time period (e.g., a time period while the user is sleeping). For example, during sleep, the force sensor may detect a user's heart rate. A graph displaying the user's heart rate while the user was sleeping may be generated and may be displayed on, for example, a display of an external electronic device.

Figure 3:
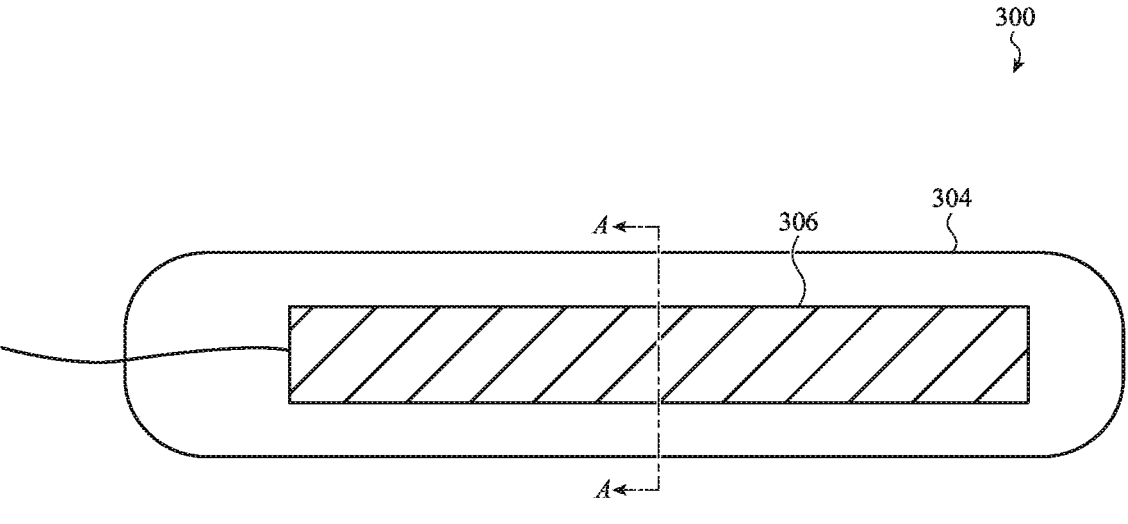
FIG. 3 depicts an example force sensor that may be used to detect biological vibrations.

FIG. 3 depicts an example cut-away view of a sensing package 300 in accordance with aspects of the provided disclosure. In particular, the sensing package 300 shown in FIG. 3 includes a piezoelectric sensor 306, which may be equivalent to the force sensor 106. The piezoelectric sensor 306 may be encapsulated in a housing 304, which may be a flexible housing. In some embodiments, the housing 304 includes an adhesive, hook-and-loop fastener, and so on and can be affixed to a surface such as a mattress surface. In use, the piezoelectric sensor 306 may be positioned to align with a user's torso. In alternate scenarios, the piezoelectric sensor 306 is positioned at a different location and/or oriented in a different direction with respect to a user's torso or other body part.

The sensing package 300 may include wiring, electrical traces, and so on, to provide power to the piezoelectric sensor 306, as depicted on the left-side of FIG. 3. The wiring may couple a plug with the piezoelectric sensor 306. The plug may, in turn, be coupled with an electrical output thereby providing power to the piezoelectric sensor 306. The wiring may additionally transport electrical signals, corresponding to biological vibrations captured by the piezoelectric sensor 306, to an external location. In some embodiments, the wiring is removed and a battery is provided within the housing 304.

The piezoelectric sensor 306 may comprise microstructures, as described below with respect to FIGS. 4-6C, which may be positioned or used to sense the same or different biological vibrations within particular biological ranges of interest. Different microstructures, or sets of microstructures, may be tuned to resonate within different biological ranges of interest corresponding to different biological vibrations and may be included in a single piezoelectric sensor 306 as well as being formed on a single substrate of such a sensor.

In an example, a first array of microstructures of the piezoelectric sensor 306 are located proximate to a person's chest in an area corresponding to lung activity and/or are tuned to detect lung vibrations or sounds. Continuing the above example, a second array of microstructures is located proximate to a person's chest in an area corresponding to heart activity and/or tuned to detect heart vibrations or sounds. Additionally or alternatively, the microstructures may be positioned such that differently tuned microstructures are interspersed amongst one another.

The microstructures may be tuned to resonate at vibrations corresponding to particular biological ranges of interest. As one example of the foregoing, some microstructures are tuned to resonate in response to heart murmurs and other microstructures are tuned to resonate in response to BCG/SCG vibrations. With this arrangement, particular biological vibrations are amplified and isolated in order to more easily analyze the detected signals (see FIG. 8, below). Additionally, different sections, or arrays, of the force sensor may be sensitive to different biological ranges of interest. For example, by grouping multiple microstructures together that are commonly sensitive to specified frequency ranges, the output of each such microstructure are aggregated to provide an amplified signal for any given biological parameter or source (e.g., heartbeat, breathing, or snoring). In this manner, ambient sounds may be ignored by the piezoelectric sensor 306 or may be excluded from the vibrations sensed by the piezoelectric sensor 306 in instances with the ambient sounds comprise vibrations falling outside of the biological ranges of interest.

In this way, the piezoelectric sensor 306 may be used to sense various types of biological vibrations and/or sounds. As previously discussed, the sensing of biological sounds by a piezoelectric sensor can enable accurate and amplified sensing of sounds having a particular frequency bandwidth corresponding to a biological range of interest. In some cases, the sensed biological vibrations may propagate through a person and/or other objects that are directly or indirectly in contact with the force sensors, as well as the source of such vibrations.

Figure 4:
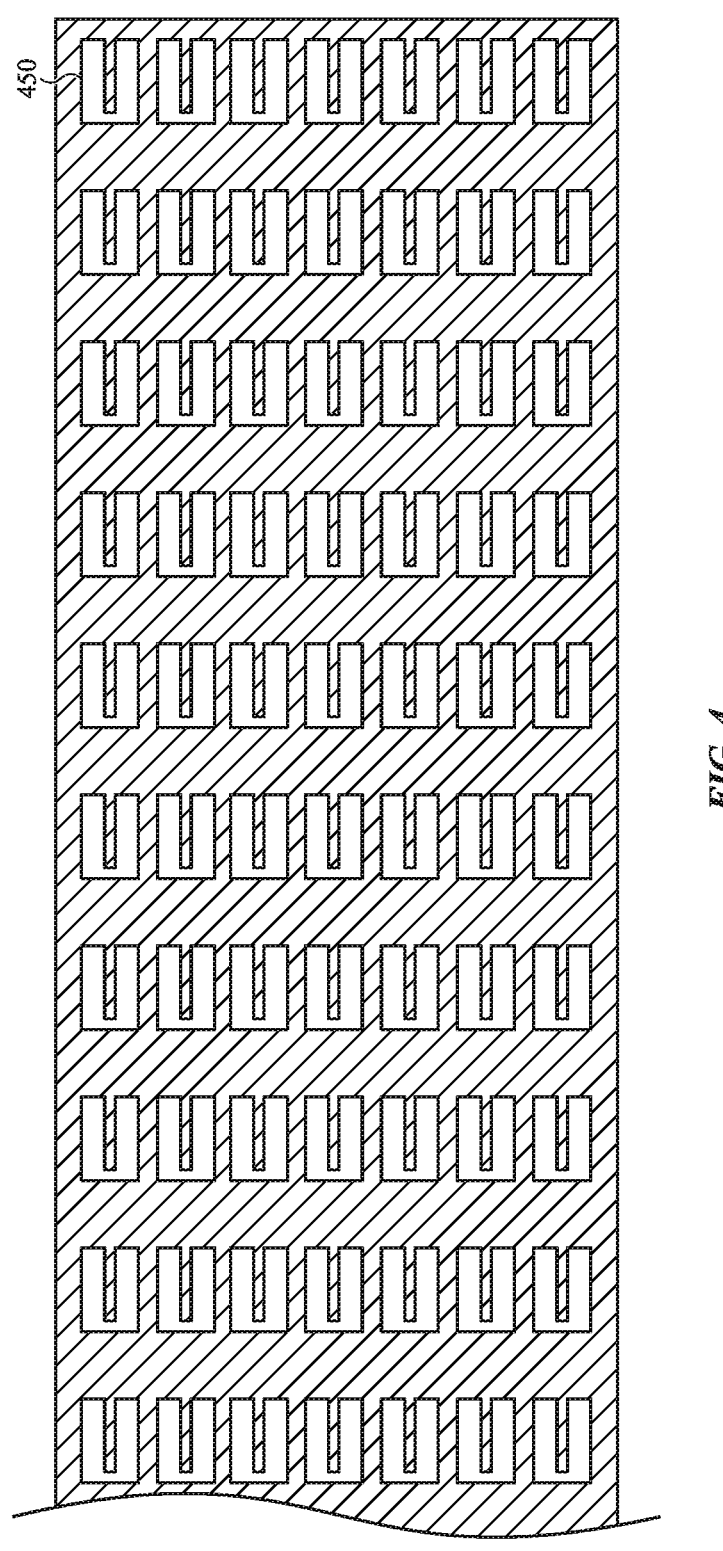
FIG. 4 depicts an example piezoelectric film including an array of microstructures, which may be used as a part of a force sensor such as described in FIG. 3.

FIG. 4 depicts a piezoelectric film 422 including an array of microstructures 450. As described herein, the piezoelectric film 422 may operate as a force sensor, or as a part of a force sensor. For example, the piezoelectric film 422 is part of a force sensor stack, as depicted and described with respect to FIG. 7.

The piezoelectric film 422 may be formed from a polyvinylidene difluoride (PVDF) material, such as a PVDF film, a PVDF-copolymer, a PVDF/poly-L-lactide (PLLA) blend, and so on. In additional or alternate cases, the piezoelectric film 422 incorporates or is formed from a PLLA material or other material.

Figure 5:
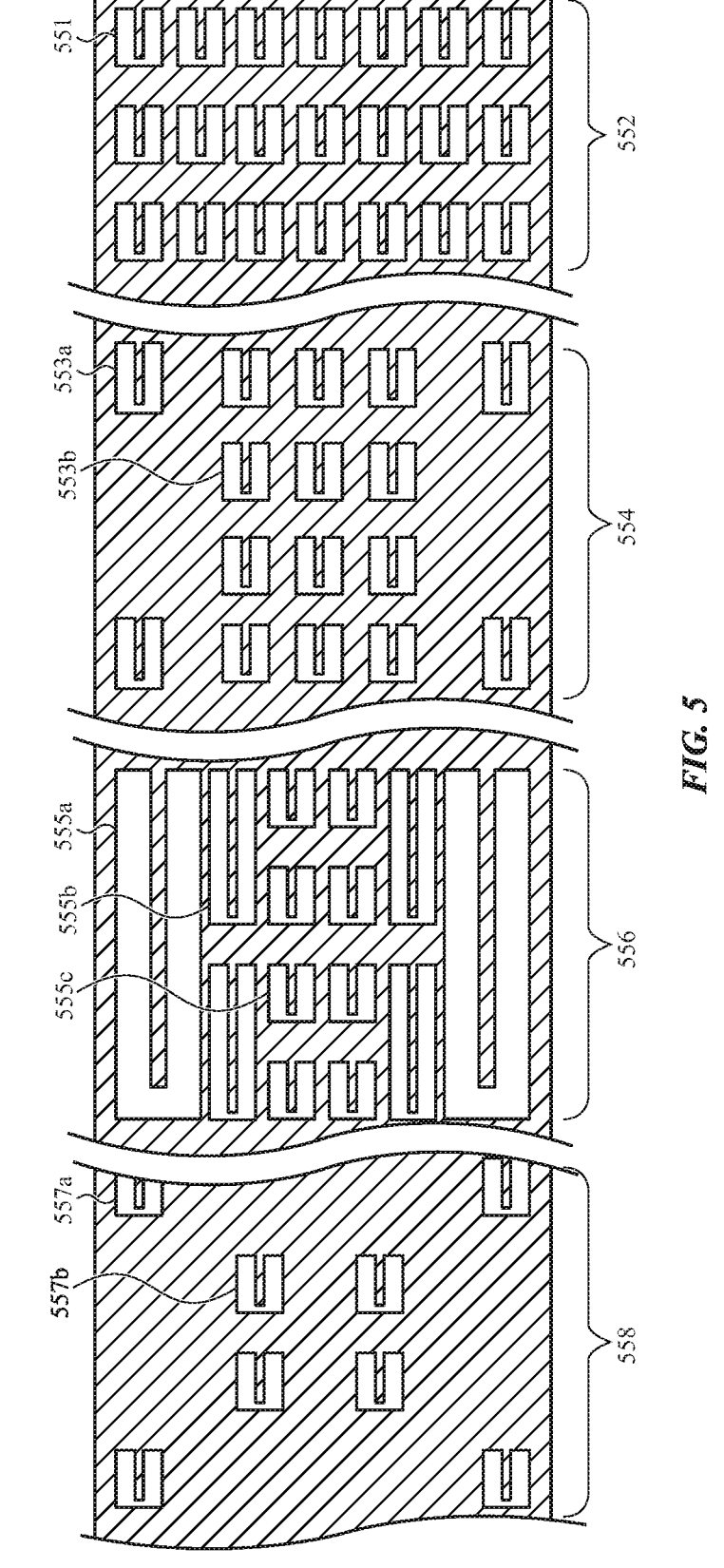
FIG. 5 depicts example alternative embodiments of different arrangements of microstructures as disposed on one or more example piezoelectric films.

As depicted in FIG. 4, an array of microstructures 450 is patterned on the surface of the piezoelectric film 422. As discussed with reference to FIG. 9, below, the array of microstructures 450 may be formed on the surface of the piezoelectric film 422 through the use of any of a number of manufacturing techniques. In various embodiments, the array of microstructures 450 are stamped, punched, drilled, etched, laser-cut, and so on to remove material within the piezoelectric film 422 to form the array of microstructures 450. In some cases, the array of microstructures 450 is a uniform, repeating grid of microstructures 450, as depicted in FIG. 4. In alternate or additional cases, microstructures are formed with different patterns, sizes, shapes, and so on, some examples of which are depicted in FIG. 5.

Each microstructure of the array of microstructures 450 may be defined by a respective hole in the piezoelectric film. For example, sections of the piezoelectric film may be cut, punched-out, or otherwise removed to define a microstructure.

Each microstructure 450 may take the form of a cantilevered portion tuned to resonate within or along a certain biological range of interest. The cantilevered portion may be tuned to a predetermined natural frequency, which may correspond to a biological region of interest. For example, a cantilevered portion is tuned to resonate within a biological range of interest of 100 Hz-1 kHz based on preselected dimensions of the cantilevered portion (see, for example, FIGS. 6A-6C). Continuing the above example, when a biological vibration, such as normal lung sounds 206, are applied to the piezoelectric film 422, the microstructure 450 tuned to the biological range of interest of 100 Hz-1 kHz oscillates at a higher amplitude than the microstructure 450 would for vibrations outside of that range. In this way, pre-amplification (e.g., amplification before signal or post-processing amplification) of certain frequencies may be achieved due to the structure and/or particular dimensions of the microstructures 450.

A given microstructure 450 may be tuned to resonate across a broader or a narrower biological range of interest. As discussed in the above example, a microstructure 450 can be tuned to resonate within a biological range of interest of 100 Hz-1 kHz, corresponding to a biological range of interest of normal lung sounds 206. In some cases, a microstructure 450 may be tuned to a specific frequency, such as a frequency of 500 Hz to primarily amplify sounds and/or biological frequencies that oscillate at or around 500 Hz. In additional or alternative cases, a given microstructure 450 is tuned across a range wider than a particular biological range of interest, such as between 100 Hz to 6 kHz. This expanded biological range of interest generally corresponds to any vibrations and/or sounds arising from a user's lungs. In such cases, the microstructure 450 amplifies any sounds or vibrations coming from a person's lungs.

Though amplification of vibrations and/or sounds arising from a user's lungs are discussed above, microstructures 450 may be tuned to any biological range of interest corresponding to any biological vibrations and/or sounds. For example, microstructures 450 can be tuned in order to amplify biological vibrations and/or sounds generated by heart movement. Microstructures 450 may additionally be tuned to amplify biological vibrations arising from blood flow, nasal vibrations, and so on.

Further, while the microstructures 450 are depicted as having a rectangular-shaped, cantilever structure, any shape, or any combination of shapes, of the microstructures 450 may be used in accordance with the provided disclosure. For example, circular, semi-circular, square, polygonal, and so on, shapes may be used as a cantilever structure and may be tuned to predefined frequencies, as discussed herein. In additional or alternative cases, a microstructure 450 may not include a cantilever structure and may instead include any geometry configured to resonate at a certain frequency or within a particular biological range of interest.

FIG. 5 depicts example alternative piezoelectric films including arrays of microstructures with varying sizes, orientations, and/or distributions. In some cases, multiple different biological ranges of interest may be amplified so as to obtain amplified information concerning a number of simultaneous biological vibrations.

FIG. 5 depicts another example piezoelectric film 522. It is noted that the piezoelectric film 522 may be one piezoelectric film or may represent multiple piezoelectric films 522. As depicted in FIG. 5, the microstructures may have any number of sizes, may be positioned in any number of arrangements, may be formed in a repeating pattern, may be interspersed amongst other microstructures, may have a higher concentration at a central portion of the piezoelectric film 522, may have a lower concentration at edge portions of the piezoelectric film 522, and so on. The particular arrangement of microstructures on the one or more piezoelectric films 522 are provided for explanatory purposes and any conceivable arrangement may be used in accordance with the provided disclosure.

As depicted in FIG. 5, each respective arrangement (e.g., a first arrangement 552, a second arrangement 554, a third arrangement 556, and a fourth arrangement 558) does not overlap with a neighboring arrangement. However, in some cases, neighboring arrangements do overlap.

In accordance with some examples, microstructures are arranged in a first arrangement 552, a second arrangement 554, a third arrangement 556, and/or a fourth arrangement 558. In some cases, each of the first, second, third, and fourth arrangements 552, 554, 556, and 558 are formed on a single piezoelectric film 522. In additional or alternative cases, one arrangement (e.g., the second arrangement 554) is formed on a single piezoelectric film 522 such that the arrangement extends across a length of the piezoelectric film 522. Any number or combination of arrangements may be formed on a single piezoelectric film 522 and the distribution of the arrangements is not limited to any particular embodiment. Further, each arrangement may be tuned to a particular biological range of interest, such that a single piezoelectric film 522 has multiple regions that are tuned differently.

In a first arrangement 552, the piezoelectric film 522 comprises an equally-spaced array of identically tuned first microstructures 551. As discussed with reference to FIG. 4, the first microstructures 551 may be tuned to resonate within a particular biological range of interest so as to amplify, for example, sounds or biological vibrations coming from a user's lungs. In some cases, the microstructures 551 are equally spaced, but are tuned to a number of different biological ranges of interest. For example, some microstructures 551 (e.g., microstructures of a first array of microstructures) are tuned to a first biological range of interest that resonates in response to biological vibrations coming from a user's lungs and other microstructures 551 (e.g., a second array of microstructures) are tuned to a second biological range of interest that resonates in response to biological vibrations coming from a user's heart.

In a second arrangement 554, a first concentration of first microstructures 553*a* may be lower at edge portions of the piezoelectric film 522 and a second concentration of second microstructures 553*b* may be greater at a center portion of the piezoelectric film 522. When the piezoelectric film 522 is used within a force sensor (e.g., the force sensor 106), the piezoelectric film 522 may be installed with a particular orientation on a surface (e.g., the bed 102). In accordance with the orientation of the piezoelectric film 522, certain regions of the piezoelectric film 522 may receive stronger, or weaker, biological vibrations. For example, an edge portion of the piezoelectric film may receive strong biological vibrations and a center portion may receive weak biological vibrations. To enable consistent vibration detection across the entire second arrangement 554 of the piezoelectric film 522, therefore, regions where stronger biological vibrations are received (corresponding to the first concentration of first microstructures 553*a* at the edges of the piezoelectric film 522) may have a lower concentration of microstructures and regions where weaker biological vibrations are received (corresponding to the second concentration of second microstructures 553*b* at the center of the piezoelectric film 522) may have a higher concentration of microstructures.

Additionally of alternatively, the types of biological vibrations imparted on the piezoelectric film 522 may differ across the surface of the piezoelectric film 522. For example, heart vibrations may typically impact a center portion of the piezoelectric film and lung vibrations may typically impact an edge portion of the piezoelectric film. In such cases, the second arrangement 554 may be used such that the first microstructures 553*a* are tuned to capture lung sounds and the second microstructures 553*b* are tuned to capture heart sounds. A concentration of the respective first microstructures 553*a* and the second microstructures 553*b* may additionally vary based on the expected vibrations.

Continuing the above example, lung activity may result in stronger vibrations when compared with vibrations arising from heart activity. A first concentration of first microstructures 553*a* may be higher than a second concentration of second microstructures 553*b*, to facilitate detecting vibrations arising from, for example, heart activity.

The second microstructures 553*b* may be tuned to detect any kind of biological vibration not limited to heart vibrations, such as lung vibrations, nasal vibrations, blood flow vibrations, and so on. The first microstructures 553*a* may additionally be tuned to detect any kind of biological vibration not limited to lung vibrations, such as heart vibrations, nasal vibrations, blood flow vibrations, and so on.

In a third arrangement 556, microstructures may include microstructures of varying sizes, such that the larger microstructures 555*a* are positioned in edge areas of the piezoelectric film 522 and the smaller microstructures 555*c* are positioned in center areas of the piezoelectric film 522. Additionally, mid-sized microstructures 555*b* may be located in between the larger microstructures 555*a* and the smaller microstructures 555*c*. In accordance with acoustic principals, larger microstructures 555*a*, referencing microstructures having a cantilever portion with a longer length, may resonate at frequencies lower than smaller microstructures 555*c*. Further, the mid-sized microstructures 555*b* may resonate at frequencies in between respective resonating frequencies at the larger microstructures 555*a* and the smaller microstructures 555*c*. As such, in the third arrangement 556, higher frequency signals may be detected by the larger microstructures 555*a*, lower frequency signals may be detected by the mid-sized microstructures 555*b*, and the lowest frequency signals may be detected by the smaller microstructures 555*c*.

The fourth arrangement 558 is a further example of an arrangement of first microstructures 557*a* and second microstructures 557*b*. The fourth arrangement 558 may be similar to the second arrangement 554, but may utilize fewer microstructures (e.g., at a center portion of the piezoelectric film 522). Any of the arrangements 552, 554, 556, and 558 may be used in isolation or in combination with other arrangements, with respect to a single piezoelectric film 522. In some embodiments, each or some of the arrangements 552, 554, 556, and 558 may be interspersed amongst each other. Additional, undepicted arrangements may additionally be patterned on a surface of the piezoelectric film 522 in accordance with acoustic principles and to amplify detected frequencies within a particular biologic range of interest.

Though specific arrangements of microstructures are discussed with respect to FIGS. 4 and 5, it is noted that any arrangement of microstructures may be used to amplify one or more frequencies corresponding to biological vibrations, or other vibrations or sounds.

Figure 6A:
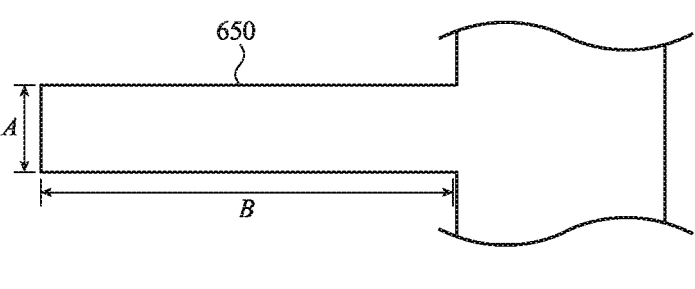
FIG. 6A depicts a top-down view of an example microstructure such as depicted in FIG. 3.
Figure 6B:
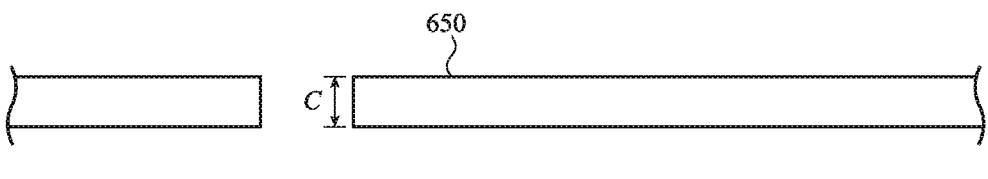
FIG. 6B depicts a side view of the example microstructure of FIG. 6A.
Figure 6C:
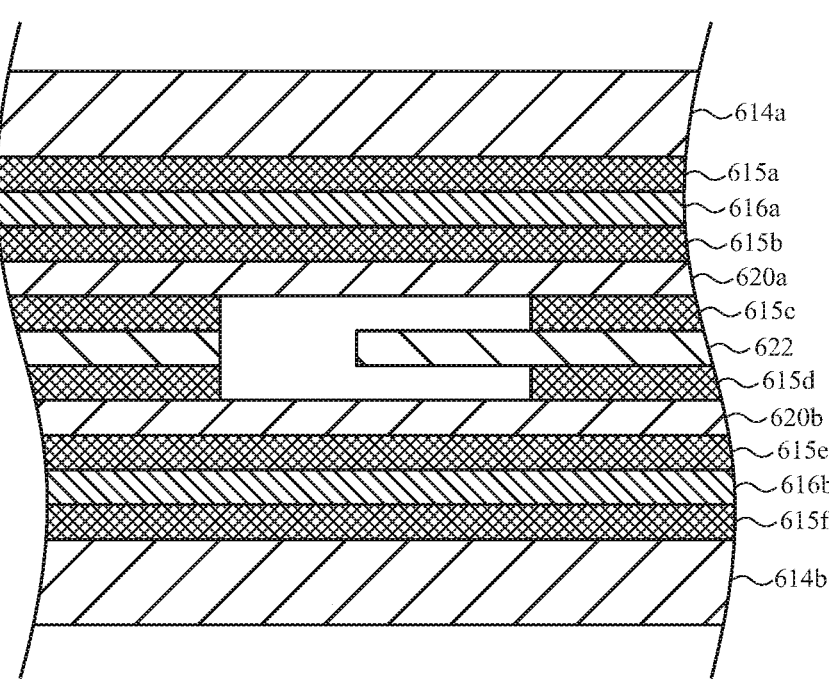
FIG. 6C depicts the example microstructure of FIGS. 6A and 6B as provided in an example force sensor stack-up.

FIGS. 6A-6C depict an expanded view of a microstructure 650, which may correspond to any previously described microstructure such as microstructures 450 and microstructures depicted in FIG. 5. FIG. 6A depicts a top-down view of the microstructure 650 and FIG. 6B depicts a side view of the microstructure 650. FIG. 6C depicts a cross-section of a piezoelectric sensor and may be a cross-section taken across line A-A as depicted in FIG. 3.

FIG. 6A depicts a microstructure 650 having a width A and a length B with respect to a cantilever portion. In some cases, the cantilever portion is any portion of the microstructure 650 which vibrates at a particular resonant frequency. The width A and the length B may be predetermined and preselected before formation of the microstructure 650 and may be selected based on acoustic principals. The width A and the length B may be set in accordance with a material of the piezoelectric film to cause the microstructure to resonate at a frequency corresponding to a biological range of interest of, for example, 100 Hz-1 kHz. The width A and the length B may alternatively be set in order to have the cantilever portion resonate at any frequency, or biological range of interest, corresponding to biological vibrations or sounds. In FIG. 6A, the length B is depicted as larger than the width A, though in some cases the width A is larger than the length B. The dimensions of the width A and/or the length B may be within any scale, including the centimeter, millimeter, micrometer, and so on scales. As a non-limiting example, the width A is within a range of 5 micrometers-100 micrometers and the length B is within a range of 30 micrometers-600 micrometers, though any other dimension may be used in accordance with the provided disclosure.

The width A and the length B of a microstructure 650 may be equivalent for all such microstructures in an array of microstructures. For example, in the embodiment depicted in FIG. 4, each microstructure 450 has equivalent widths and lengths. In alternative cases, the width A and the length B may be different for certain microstructures, as depicted in, for example, FIG. 5. As discussed above, different arrangements or arrays of microstructures may be tuned to different resonant frequencies and may amplify different biological vibrations. This tuning process may reference changing geometric values of a microstructure 650, including, but not limited to, changing dimensions of the width A and the length B. In some cases, tuning the microstructure 650 may reference changing a material and/or a thickness of the microstructure 650.

FIG. 6B depicts a side view of the microstructure 650, depicting a thickness C of the microstructure 650. The thickness C may be modified to control or set a resonance of the microstructure 650, as discussed above with reference to width A and length B, or may be the same as a thickness of a piezoelectric film from which the microstructures are formed. Each of the width A, length B, and/or thickness C may be or may define tuning parameters of the microstructure 650 and may be modified, selected, or calculated to result in a particular resonance of the microstructure 650. Other examples of tuning parameters include a periodicity of the microstructure 650 (in relation to surrounding microstructures, such as depicted in FIGS. 4 and 5), a stiffness, such as a material stiffness, of the microstructure, an orientation of the microstructure, a layout of the microstructure, and so on. Each tuning parameter, either individually or collectively, can be varied to change resonance selection of one or more microstructures.

FIG. 6C depicts an example of a force sensor 606 taken along line A-A of FIG. 3. For ease of depiction, housing layers are omitted in FIG. 6C, though a housing may surround the force sensor 606 in some embodiments. The force sensor 606 may be a piezoelectric sensor configured to detect forces and/or vibrations arising from biological sounds or vibrations.

The outermost or exterior layers of the force sensor 606 may include a top cover film 614a and a bottom cover film 614b. The top cover film 614a and the bottom cover film 614b may be formed from a thermoplastic polymer resin, such as polyethylene terephthalate (PET) or a biaxially-oriented polyethylene terephthalate (BoPET), or from any other resin, plastic, or material configured to act as a top and bottom layer of the force sensor 606. The top cover film 614a and the bottom cover film 614b may be considered first and second non-conductive stack covers for the force sensor 606. In some cases, a thickness of the top cover film 614a and the bottom cover film 614b is about 75 micrometers, though the thickness is not limited to any particular value. Alternatively, the top cover film 614a and the bottom cover film 614b may be omitted and a first shielding film 616a and a second shielding film 616b may be provided as outer layers of the force sensor 606.

The top cover film 614a and the bottom cover film 614b may be respectively coupled to the first shielding film 616a and the second shielding film 616b using a first pressure-sensitive adhesive (PSA) layer 615a and a second PSA layer 615f. The PSA layers 615a and 615f may be any adhesive configured to bond adjacent layers and may comprise elastomers, such as acrylic elastomers, rubber, resins, or any other type of adhesive or adhesive material. In some cases, the PSA layers have a thickness of about 50 micrometers, though any thickness of the PSA layers may be used in accordance with the provided disclosure.

The first shielding film 616a and the second shielding film 616b may additionally be provided within the force sensor 606. The first shielding film 616a and the second shielding film 616b may be grounded (e.g., connected to an electrical ground) and may be insulated from a piezoelectric layer 622, a first electrode 620a, and a second electrode 620b. In cases where the first shielding film 616a and the second shielding film 616b are grounded, the shielding films may be connected to a common ground (e.g., a shared ground) or may be connected to different grounds. In some cases, the shielding films have a thickness of about 45 micrometers, though any thickness of the shielding films layers may be used in accordance with the provided disclosure.

The shielding films may be electromagnetic noise shields and may include, in some examples, silver (Ag), polyurethane (PU), thermoplastic polyurethane (TPU), shape-memory polymer (SMP), and so on, printed on a thermoplastic polymer resin substrate. Additionally or alternatively, the shielding films may be formed from any other suitable material which may be flexible. In some examples, an electromagnetic noise shield includes aluminum (Al) and/or copper (Cu), and/or another metal, sputtered on a thermoplastic polymer resin substrate. In some cases, an electromagnetic noise shield is formed by a conductive fabric.

The first shielding film 616a and the second shielding film 616b may be coupled to a first electrode 620a and a second electrode 620b, respectively, via a third PSA layer 615b and a fourth PSA layer 615e. The third PSA layer 615b and the fourth PSA layer 615e may comprise any kind of adhesive and may be substantially similar to the first PSA layer 615a and the second PSA layer 615f.

The first electrode 620a and the second electrode 620b may cooperate to passively output signals obtained from the piezoelectric layer 622. For example, the first electrode 620a and the second electrode 620b may output signals in accordance with a changing electrical charge within the piezoelectric layer 622. A cantilever portion of the piezoelectric layer 622 may additionally resonate in response to biological vibrations, as discussed herein. In accordance with the piezoelectric effect, where mechanical changes to a piezoelectric material result in an electrical charge, resonating portions of the piezoelectric layer 622 may generate a changing voltage and/or charge. The first electrode 620a and the second electrode 620b may detect the changing voltage and/or charge and may output a signal corresponding to the movement of the piezoelectric layer 622. In this way, motion of portions of the piezoelectric layer 622 (e.g., microstructures) may be converted into electrical signals and may be used to analyze and detect biological vibrations.

The piezoelectric layer 622 may, as discussed above, include any number of microstructures, such as cantilevered portions. These microstructures may resonate at predetermined frequencies in accordance with tuning parameters as discussed with reference to FIGS. 6A and 6B. In some cases, the piezoelectric layer 622 may be bonded to the first electrode 620a and the second electrode 620b through a fifth PSA layer 615c and a sixth PSA layer 615d, which may be similar to other PSA layers as discussed herein.

Figure 7:
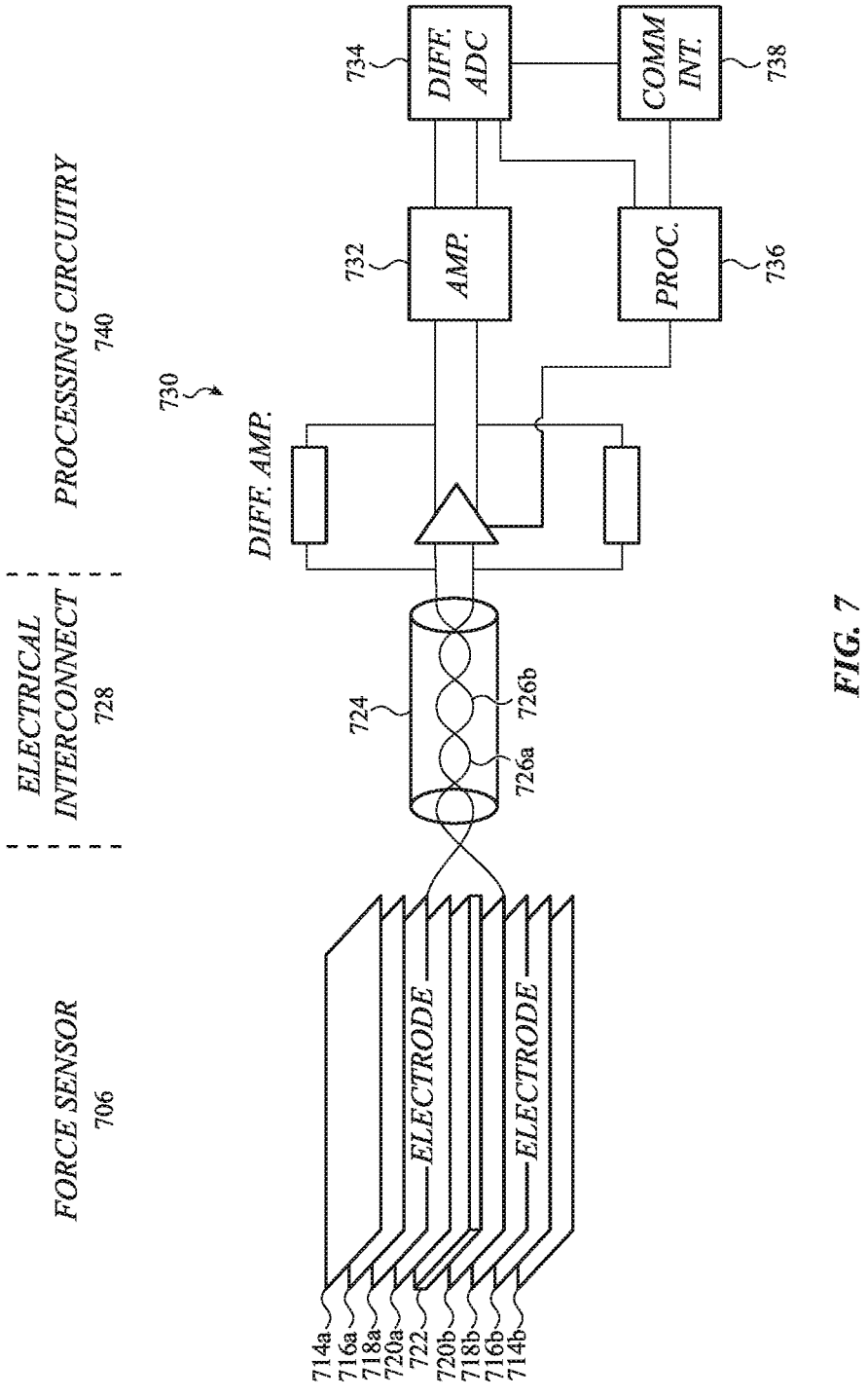
FIG. 7 depicts an example embodiment of various components included in a sensor system.

FIG. 7 depicts various components of a sensor system described with reference to FIGS. 1 and 3. In particular, FIG. 7 depicts examples of a force sensor 706, an electrical interconnect 728, and processing circuitry 740.

As depicted in FIG. 7, the force sensor 706 may comprise a stack, or stack-up, of various elements or layers stacked on top of each other. A piezoelectric layer 722 may be disposed at a core of the force sensor 706 and may include a number of microstructures provided on a surface thereof (see FIGS. 4 and 5). As described above, the piezoelectric layer 722 may be formed from a polyvinylidene difluoride (PVDF) material, such as a PVDF film, a PVDF-copolymer, a PVDF/poly-L-lactide (PLLA) blend, and so on. The piezoelectric layer 722 may alternatively be a PLLA material or other material. The piezoelectric layer 722 may have first and second opposing sides and surfaces that extend in a plane perpendicular to the force sensor 706 stack. A length of a cantilever portion of a microstructure may extend across a length of the piezoelectric layer 722, across a width of the piezoelectric layer 722, diagonally across the piezoelectric layer 722, or any combination thereof.

A first electrode 720a (e.g., a positive electrode) may be connected to the first side or surface of the piezoelectric layer 722, and a second electrode 720b (e.g., a negative electrode) may be connected to the second side or surface of the piezoelectric layer 722. The first electrode 720a and the second electrode 720b may output a pair of signals obtained from the piezoelectric layer 722 (e.g., as a result of detected forces/vibrations via vibrating microstructures) to an electrical interconnect 728. The electrical interconnect 728 may be permanently or detachably connected to the force sensor 706.

The force sensor 706 may further include a first shielding film 716a (e.g., a first ground layer) disposed on the first side of the piezoelectric layer 722 and the first electrode 720a. The first shielding film 716a may act as an electromagnetic shield and may be electrically insulated from, and may electrically insulate, both the piezoelectric layer 722 and the first electrode 720a, with the first electrode 720a disposed between the piezoelectric layer 722 and the first shielding film 716a. The force sensor 706 may also include a second shielding film 716b (e.g., a second ground layer) disposed on the second side of the piezoelectric layer 722 and the second electrode 720b. The second shielding film 716b may act as an electromagnetic shield and may be electrically insulated from, and may electrically insulate, both the piezoelectric layer 722 and the second electrode 720b, with the second electrode 720b disposed between the piezoelectric layer 722 and the second shielding film 716b.

In some cases, a first thermoplastic polymer resin 718a is disposed between the first electrode 720a and the first shielding film 716a, and a second thermoplastic polymer resin 718b is disposed between the second electrode 720b and the second shielding film 716b.

In some cases, the outermost or exterior layers (and in some cases sides) of the force sensor 706 includes a third thermoplastic polymer resin 714a disposed on or over the first shielding film 716a, and a fourth thermoplastic polymer resin 714b disposed on or over the second shielding film 716b. The third thermoplastic polymer resin 714a and the fourth thermoplastic polymer resin 714b may be considered first and second non-conductive stack covers for the force sensor. In additional or alternative cases, the first shielding film 716a and the second shielding film 716b may be the outermost or exterior layers of the force sensor 706, or the first thermoplastic polymer resin 718a and the second thermoplastic polymer resin 718b may be the outermost or exterior layers of the force sensor 706.

The first thermoplastic polymer resin 718a and the second thermoplastic polymer resin 718b may be coupled to the first electrode 720a and the second electrode 720b using a pressure-sensitive adhesive (PSA). Similarly, the third thermoplastic polymer resin 714a and the fourth thermoplastic polymer resin 714b may be coupled to the first shielding film 716a and the second shielding film 716b using a PSA, which may be deposited on each of the shielding films or on each of the thermoplastic polymer resins. Any of the thermoplastic polymer resins may alternatively be replaced with a different type of electrical insulator.

In some embodiments, the elements or layers stacked on either side of the piezoelectric layer 722 are symmetric or nearly symmetric and are on opposite sides of the piezoelectric layer 722. In some cases, layers have a symmetric projection over 90% or more of their length. The shielding films may cover most of the surface area of the electrodes, but may have respective surface areas that are greater than the surface areas of the electrodes. This may assist to mitigate or eliminate the inducement of common mode noise in the electrodes.

The electrical interconnect 728 may mechanically and electrically connect to the force sensor 706 and may include a first conductor 726a and a second conductor 726b that connect to the first electrode 720a and the second electrode 720b. The first conductor 726a and the second conductor 726b may be surrounded by insulation, and may be twisted to form a twisted pair within the electrical interconnect 728. The first shielding film 716a and the second shielding film 716b may be connected to each other and to an electromagnetic noise shield 724, such as, for example, a metal or conductive sheath, that surrounds the first conductor 726a and the second conductor 726b, thereby forming a shielded twisted pair. The electromagnetic noise shield 724 may additionally be surrounded by a non-conductive sheath, which is not depicted in FIG. 7. In additional or alternative embodiments, the first conductor 726a and the second conductor 726b may be routed on a substrate as conductive traces, with a noise shield being formed by conductive traces or planes coupled to the shielding films.

In some cases, processing circuitry 740 is additionally provided. The processing circuitry 740 may include components that form part of an analog front end and/or a data acquisition circuit. The processing circuitry 740 may include a differential amplifier 730, a differential analog-to-digital converter (ADC) 734, a communications interface 738, a processor 736, and/or other circuitry. The differential amplifier 730 may be connected to the first conductor 726a and the second conductor 726b of the electrical interconnect 728. The first conductor 726a and the second conductor 726b may be electrically connected to input nodes or terminals of the differential amplifier 730. The differential amplifier 730 may provide amplified differential output 732, such as an amplification of the pair of signals obtained from the piezoelectric layer 722. The differential output 732 may include biological vibrations sensed by the piezoelectric layer 722 and, more specifically, by microstructures on a surface of the piezoelectric layer 722.

The differential ADC 734 may be configured to digitize the differential output of the differential amplifier 730. The differential ADC 734 may combine the differential signals or differential output of the differential amplifier 730. The digitized differential output may be stored in an optional memory and/or transmitted to another device via the communications interface 738. In some cases, the communications interface 738 includes a WI-FI and/or BLUETOOTH interface. An optional processor 736 or other circuitry may control operations of the differential amplifier 730, differential ADC 734, communications interface 738, memory, and/or other components of the processing circuitry 740.

The processor 736 of the processing circuitry 740 may identify at least a first vibration included in the digitized differential output of the differential ADC 734. The same or a different processor may then pattern match the first vibration to any of a number of known biological vibrations, including, for example, any of the biological vibrations described with reference to FIG. 2.

The processing circuitry 740 may receive signals corresponding to one output, such as a combined output, of the force sensor 706. For example, even in instances where multiple arrays/types of microstructures amplify different biological ranges of interest, one combined signal may be produced via the processing circuitry 740 (see FIG. 8). The total response of the force sensor 706, therefore, may be a supposition of all the microstructures on a piezoelectric film as well as the piezoelectric film's strain response. Additional circuits may be provided to separate signals received from different types of microstructures. For example, a unique circuit may be provided with respect to a first array of microstructures and may analyze/receive signals corresponding to a first kind of biological vibration. Continuing the above example, a second unique circuit may be provided with respect to a second array of microstructures.

Figure 8:
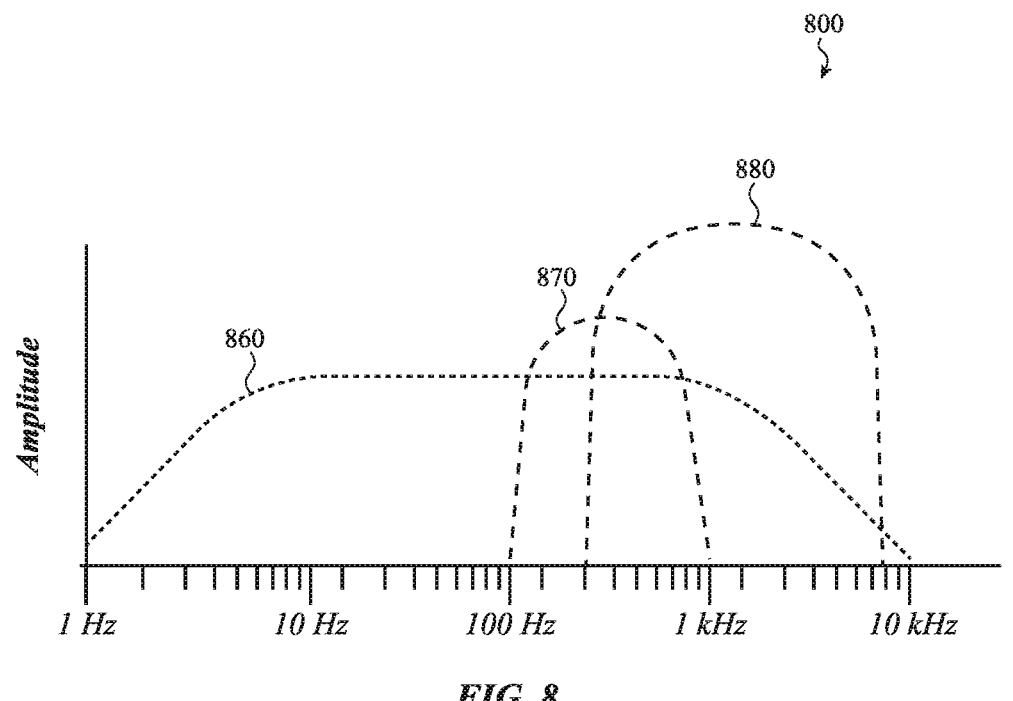
FIG. 8 illustrates an example graph including a sensor film response and amplified vibrational signals as captured by a first type of microstructure and a second type of microstructure.

FIG. 8 illustrates an example sensor response 800 as may be received from a force sensor in accordance with the provided disclosure. The curve 860 references a frequency response of a piezoelectric film, that is, a frequency response due to the planar structure of the piezoelectric film. The curve 860 may be an amplitude of a received biological vibration across a certain frequency range. For example, a material and structure of the piezoelectric film may result in a relatively consistent response across 10 Hz-1 kHz, with a somewhat lower response occurring at an edge of the range (e.g., below 10 Hz and above 1 kHz). This may be referenced as a "flat" sensor response. The curves 870 and 880 reference pre-amplified signals that arise due to the microstructures previously described. For example, the curve 870 may result from microstructures that amplify biological vibrations in the 100 Hz-1 kHz biological range of interest and the curve 880 may result from microstructures that amplify biological vibrations in the 300 Hz-8 kHz biological range of interest. It is noted that sensor response 800 may depict the force sensor response before any post-signal processing occurs. In other words, the sensor response 800 depicts amplified signals due primarily to the structure of the microstructures provided on a surface of a piezoelectric film.

Figure 9:
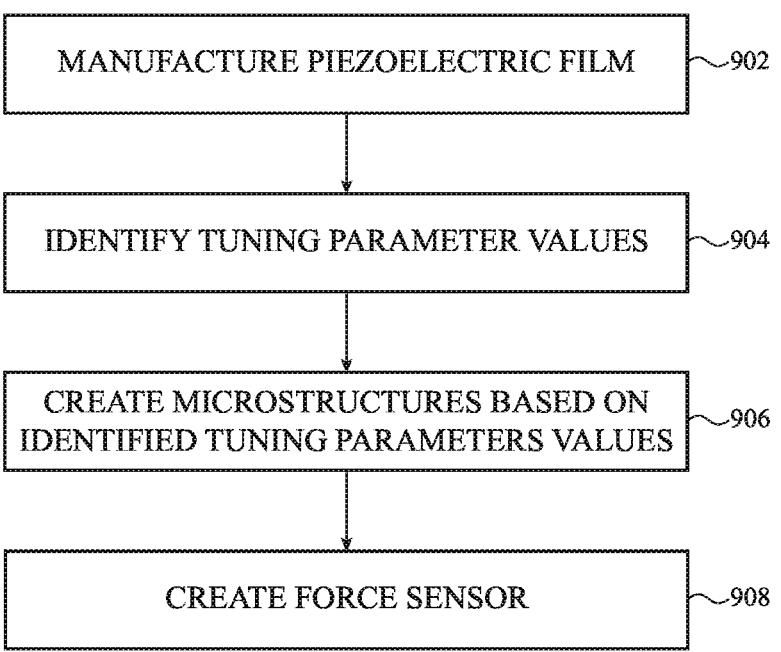
FIG. 9 depicts a flowchart providing operations for a method of fabricating and manufacturing a piezoelectric film and microstructures positioned on a surface of the piezoelectric film in accordance with aspects of the provided disclosure.

FIG. 9 illustrates a method 900 of manufacturing microstructures of a piezoelectric film in accordance with aspects of the provided disclosure.

At operation 902, a piezoelectric film may be manufactured in accordance with traditional manufacturing techniques. The piezoelectric film may have a flat sensor response, so as to not amplify any particular biological vibration. An example of the flat sensor response is depicted as curve 860 in FIG. 8.

At operation 904, tuning parameters may be identified. The tuning parameters may be identified based on biological vibrations which are desirably amplified. For example, in situations where biological vibrations corresponding to lung vibrations and/or sounds are to be mechanically amplified, tuning parameters may be selected which result in microstructures resonating (e.g., a natural resonance) between 100 Hz-6 kHz. As described above, tuning parameters may correspond to a dimension of the microstructures, a shape of the microstructures, an orientation of the microstructures, and so on. Any such tuning parameter, or combination of tuning parameters, may be varied. In some cases, multiple biological vibrations are desirably amplified and different arrays of microstructures may be tuned differently. Further, different patterns of microstructures may be identified.

At operation 906, one or more arrays of microstructures may be formed on the piezoelectric film using the tuning parameters identified at operation 904. The microstructures may be formed through any method of forming structures on a film including such methods as discussed above. The piezoelectric film may be stamped, cut, drilled, laser-cut, and so on to form the microstructures. As described above, one type of microstructure may be formed to amplify one type of biological vibration or many types/arrays of microstructures may be formed to amplify multiple types of biological vibrations. At operation 908, a force sensor, including a piezoelectric film, one or more electrodes, one or more shielding films, and so on, may be created.

The force sensors described herein may be used to opportunistically monitor a user's heart rhythm, by sensing basic heart vibrations (S1 and S2 heart sounds) and/or BCG/SCG vibrations. An irregular rhythm may be detected by pattern matching S1/S2 and/or BCG/SCG heart vibrations to known and/or learned arrhythmia vibration patterns.

The force sensors described herein may further be used to classify a user's heart rhythm (e.g., as regular (a sinus rhythm (SR)), irregular (atrial fibrillation), inconclusive, and so on). The force sensors described herein may be used to generate a report of a user's heart rate variability (HRV).

The force sensors described herein may be used to monitor symptoms associated with asthma (e.g., coughs, wheezes, or nighttime awakenings) and generate, for example, a nightly index, trends by week, month, or other time period, and so on. Incidences of a particular biological vibration or event may be counted. For example, a number of cough sounds, wheeze sounds, or snoring episodes may be counted by a processor or other circuit as a user sleeps.

The foregoing description, for purposes of explanation, uses specific nomenclature to provide a thorough understanding of the described embodiments. However, it will be apparent to one skilled in the art, after reading this description, that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art, after reading this description, that many modifications and variations are possible in view of the above teachings.

As described above, one aspect of the present technology is the gathering and use of data available from various sources, including data that may be indicative of a user's biological vibrations or sounds, and/or data that may identify the person from which such biological vibrations or sounds were obtained. The present disclosure contemplates that, in some instances, this gathered data may include personal information data that uniquely identifies a user or can be used to identify, diagnose, classify, locate, or contact a specific person. Such personal information data can include demographic data, location-based data, telephone numbers, email addresses, home addresses, data or records relating to a user's health or level of fitness (e.g., vital sign measurements, medication information, exercise information), date of birth, or any other identifying or personal information.

The present disclosure recognizes that the use of such personal information data, in the present technology, can be used to the benefit of users. For example, the personal information data can be used to activate or deactivate various functions of a user's device, or gather health, medical, or fitness information that may be used to diagnose or assist the user. Further, other uses for personal information data that benefit the user are contemplated by the present disclosure. For instance, health, medical, and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services or anytime thereafter. In another example, users can select not to provide health, medical, or fitness data to targeted content delivery services. In yet another example, users can select to limit the length of time personal information data is maintained or entirely prohibit the development of a diagnosis based on such personal information data. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

What is claimed is:

1. A sensor system for sensing a biological vibration, comprising:
   a sensor stack comprising:
      a piezoelectric film having a first side opposing a second side and comprising an array of microstructures, each microstructure of the array of microstructures formed from a respective portion of the piezoelectric film and configured to vibrate about the piezoelectric film with a respective resonant frequency tuned to resonate within a biological range of interest corresponding to the biological vibration;
      a first electrode connected to the first side of the piezoelectric film; and
      a second electrode connected to the second side of the piezoelectric film, the first electrode and the second electrode converting the biological vibration detected by at least one microstructure of the array of microstructures into electrical signals.

2. The sensor system of claim 1, wherein:
   each microstructure of the array of microstructures has a cantilever structure; and
   the cantilever structure is tuned to amplify detection of the biological vibration.

3. The sensor system of claim 1, wherein:
   the sensor stack further comprises:
      a first shielding film coupled to the first electrode; and
      a second shielding film coupled to the second electrode;
   the first electrode is disposed between the piezoelectric film and the first shielding film; and
   the second electrode is disposed between the piezoelectric film and the second shielding film.

4. The sensor system of claim 1, wherein:
   the array of microstructures is a first array of first microstructures;
   the biological range of interest is a first biological range of interest;
   the piezoelectric film further comprises a second array of second microstructures;
   each of the second array of second microstructures is tuned to a second biological range of interest; and
   the second biological range of interest is different from the first biological range of interest.

5. The sensor system of claim 4, wherein:
   the first biological range of interest corresponds to lung vibrations in a first range of 50 Hertz to 2500 Hertz; and
   the second biological range of interest corresponds to heart vibrations in a second range of 20 Hertz to 500 Hertz.

6. The sensor system of claim 4, wherein microstructures of the first array of first microstructures and microstructures of the second array of second microstructures are formed in an alternating pattern on the piezoelectric film.

7. The sensor system of claim 4, wherein:

the first array of first microstructures are formed within a first area of the piezoelectric film;

the second array of second microstructures are formed within a second area of the piezoelectric film; and the first area does not overlap with the second area.

8. The sensor system of claim 1, wherein the array of microstructures are formed as a repeating grid of microstructures on the piezoelectric film.

9. The sensor system of claim 1, wherein the piezoelectric film is formed from a polyvinylidene difluoride material.

10. The sensor system of claim 1, further comprising a communications interface configured to transmit the electrical signals to an external electronic device.

11. A sensor system for monitoring biological vibrations generated by a user, comprising:

a flexible sensor detecting the biological vibrations from the user while the user is in contact with the flexible sensor, the flexible sensor comprising:

a flexible piezoelectric film comprising an array of microstructures, each microstructure of the array of microstructures defining a respective hole of the flexible piezoelectric film and having a respective cantilevered structure formed from a respective segment of the flexible piezoelectric film, the respective cantilevered structure amplifying detected vibrations within a biological range of interest; and a first electrode and a second electrode, respectively connected to a first surface of the piezoelectric film and a second surface of the piezoelectric film, the first surface opposing the second surface.

12. The sensor system of claim 11, wherein each microstructure of the array of microstructures is tuned to resonate at a frequency corresponding to at least one of heart vibrations or lung vibrations.

13. The sensor system of claim 11, wherein microstructures of the array of microstructures are more concentrated at a center portion of the piezoelectric film than at an edge portion of the piezoelectric film.

14. The sensor system of claim 11, wherein:

the array of microstructures comprises:

a first set of microstructures comprising first microstructures; and a second set of microstructures comprising second microstructures; and the first microstructures have a larger size than the second microstructures.

15. The sensor system of claim 14, wherein:

the first set of microstructures is positioned at an edge portion of the piezoelectric film; and the second set of microstructures is positioned at a center portion of the piezoelectric film.

16. The sensor system of claim 14, wherein:

the array of microstructures additionally comprise a third set of microstructures comprising third microstructures; and the third microstructures have a smaller size than the first microstructures and the second microstructures.

17. The sensor system of claim 16, wherein:

the first microstructures of the first set of microstructures are tuned to detect first frequencies within a first biological range of interest;

the second microstructures of the second set of microstructures are tuned to detect second frequencies within a second biological range of interest, the second frequencies higher than the first frequencies; and the third microstructures of the third set of microstructures are tuned to detect third frequencies within a third biological range of interest, the third frequencies higher than the second frequencies.

18. The sensor system of claim 11, further comprising:

a differential amplifier electrically connected to the first electrode and the second electrode and providing a differential output indicative of the detected vibrations sensed by the array of microstructures of the piezoelectric film.

* * * * *